United States Patent [19]

Mannsfeld et al.

[11] 4,069,251

[45] Jan. 17, 1978

[54] CONTINUOUS PROCESS FOR THE MANUFACTURE OF METHIONINE

[75] Inventors: Sven Peter Mannsfeld; Arno Pfeiffer, both of Bruhl; Herbert Tanner, Grossauheim; Hans Wagner, Constance, all of Germany; Erich Liebetanz, deceased, late of Mainz, Germany, by Eva Angela Liebetanz, heiress

[73] Assignee: Deutsche Gold- und Silber-Scheideanstalt vormals Roessler, Frankfurt am Main, Germany

[21] Appl. No.: 713,822

[22] Filed: Aug. 12, 1976

Related U.S. Application Data

[63] Continuation-in-part of Ser. No. 328,106, Jan. 30, 1973, abandoned, which is a continuation of Ser. No. 9,458, Feb. 6, 1970, abandoned.

[30] Foreign Application Priority Data

Feb. 8, 1969 Germany .............................. 1906405

[51] Int. Cl.² .......................................... C07C 149/247
[52] U.S. Cl. ................................................. 260/534 S
[58] Field of Search ....................................... 260/534 S

[56] References Cited

U.S. PATENT DOCUMENTS

| 2,557,920 | 6/1951 | White | 260/534 C |
| 3,668,221 | 7/1967 | Shima et al. | 260/534 S |

FOREIGN PATENT DOCUMENTS

| 40-10211 | 5/1965 | Japan | 260/534 |
| 43-19530 | 8/1968 | Japan | 260/534 |
| 630,139 | 10/1949 | United Kingdom | 260/534 S |

*Primary Examiner*—James O. Thomas, Jr.
*Assistant Examiner*—Michael Shippen
*Attorney, Agent, or Firm*—Michael J. Striker

[57] ABSTRACT

In a continuous process 5-(β-methylmercaptoethyl)-hydantoin is subjected to hydrolysis at an elevated temperature and elevated pressure in an aqueous solution of alkali carbonate or alkali bicarbonate or a mixture of these two compounds. The ammonia and carbon dioxide which form during the hydrolysis are removed and when the hydrolysis is complete the methionine is separated by means of carbon dioxide and the mother liquor is recirculated into the process after replenishing with fresh amounts of said hydantoin.

11 Claims, No Drawings

CONTINUOUS PROCESS FOR THE MANUFACTURE OF METHIONINE

CROSS-REFERENCE TO RELATED APPLICATIONS

The present application is a continuation-in-part of application Ser. No. 328,106, now abandoned filed Jan. 30, 1973 which, in turn, is a continuation of application Ser. No. 9,458, now abandoned filed Feb. 6, 1970.

BACKGROUND OF THE INVENTION

The present invention relates to a continuous process for the manufacture of methionine [α-amino-γ-methyl-mercaptobutyric acid].

Methionine has already been made by hydrolysis of 5-(β-methylmercaptoethyl)-hydantoin. The hydrolysis is carried out by heating the hydantoin, possibly under pressure, in the presence of water and specific alkaline materials. There is thus formed a solution of a methionine salt from which the pure methionine is obtained by precipitation when neutralizing the solution with an acid.

The hydrolysis has also been carried out in the reverse manner, that is by means of an acid while the subsequent precipitation of the methionine was effected by neutralization with alkali.

The alkali used in these processes were alkali- or earth alkali hydroxides such as sodium or barium hydroxide and the acids were sulphuric acid or hydrochloric acid (British patent No. 630,139).

It has also been proposed to use as alkali sodium or potassium carbonate and to use as acid a lower aliphatic carboxylic acid such as acetic acid (German patent No. 891,259).

Another proposal has been to effect the reaction of 5-alkyl substituted hydantoins by means of alkali mixtures of alkali carbonate and alkali hydroxide and to use carbon dioxide as the acid (Japanese published application 19530/68).

During the hydrolysis there are formed gaseous products. A more recent proposal is to effect the removal of these gaseous products during the reaction from the system in order to increase the yield of methionine (Netherland published application No. 65 16950).

In all these processes there occurs a substantial amount of unwanted salts formed in the neutralization which depending on the type of alkalis and acids may for instance be alkali- or earth alkali sulfates, alkali chlorides, alkali acetates or alkali bicarbonates. The separation of the methionine and the purification from these unwanted salts which may be present in a multiple molar excess causes substantial difficulties particularly if the methionine is to be obtained in a high yield.

Another shortcoming of the prior art processes is the fact that there is a continuous using up of alkali and acid. The formed salts are hardly useful. Their separation from the mother liquor is normally not worth the effort and they are therefore usually discarded together with the mother liquor. This results in substantial amounts of sewage water.

Together with the mother liquor there are also always lost certain amounts of methionine.

It is therefore an object of the present invention to avoid these shortcomings of the prior art.

SUMMARY OF THE INVENTION

In the process of the invention 5-(β-methylmercapto-ethyl)-hydantoin is subjected to hydrolysis at an elevated temperature at elevated pressure in an aqueous solution of (a) alkali carbonate or (b) alkali bicarbonate or (c) a mixture of these two compounds. The ammonia and carbon dioxide formed during the hydrolysis are removed and after completion of the hydrolysis the methionine is separated by means of carbon dioxide while the mother liquor containing the alkali bicarbonate is recirculated into the process after being replenished with fresh amounts of said hydantoin.

DESCRIPTION OF THE PREFERRED EMBODIMENTS

The hydrolysis involves a splitting off of ammonia and carbon dioxide from the hydantoin. The ammonia and carbon dioxide are volatile under the conditions of the reaction and escape from the reaction mass together with the water vapor. Carbon dioxide in addition is liberated from the alkali bicarbonate of the solution by formation of methionine. There remains in the end an alkaline solution with a pH value above 11 in which the methionine is present as alkali methioninate. In order to effect the separation of the methionine, carbon dioxide is then introduced into the solution. This may be done at an increased pressure. This will lower the pH of the solution; in general the pH will adjust to a value between 7.2 and 7.5 and the alkali methioninate will thus be converted to the less soluble methionine. Instead of gaseous carbon dioxide it is also possible to use liquid carbon dioxide or dry ice. The methionine then precipitates and can be removed without difficulty by filtering the mother liquor. It is thus obtained in a purity in excess of 99%.

The mother liquor that remains after removing the methionine is recirculated into the process and can again be used for hydrolysis of further amounts of hydantoin. Accordingly no drainage water occurs apart from small amounts of mother liquor which intermittently may be disposed of in order to avoid an accumulation of contaminations. Since residual methionine and alkali carbonate or alkali bicarbonate can also be separately recovered and recycled, the loss in these materials is extremely small. The total yield of methionine is up to 99%.

It is possible also to recirculate completely the materials that escape during the hydrolysis, that is ammonia, carbon dioxide and water. The ammonia can be used with a corresponding portion of carbon dioxide in the aqueous solution to form hydantoin from β-methylmercaptopropionaldehyde cyanhydrin. The remaining portion of the carbon dioxide can be used in order to precipitate the methionine from the reaction mass.

Both aqueous alkali carbonate solutions and alkali bicarbonate solutions and mixtures thereof can be used in the process of the invention. It is preferred to circulate the mother liquor which after elimination of the methionine essentially consists of a bicarbonate solution because of the separation with carbon dioxide and in addition may contain about 20 to 50 grams residual methionine in solution per liter which could not be separated during the precipitation but may remain. The solution is replenished prior to recycling by fresh hydantoin.

The preferred alkali bicarbonate and carbonate are the potassium salts. The ratio between hydantoin and alkali may be between 1:1 and 1:5. Preferably it should be between 1:2 and 1:3.

The temperature range for the hydrolysis of the hydantion may be between 120° and 220° C and preferably is between 140° and 180° C. The pressure is increased above atmospheric pressure corresponding to the temperature employed. Normally the pressure should be only slightly higher than the vapor pressure of the water at this temperature. The preferred pressure during the hydrolysis reaction is between 5 and 12 atm. above atmospheric.

The elimination of the ammonia and carbon dioxide that form during the hydrolysis is improved by passing water vapor or an inert gas such as nitrogen through the reaction mass. If necessary the final reaction solution from which ammonia has been removed can be decolorized or bleached by means of activated carbon. The carbon dioxide which is introduced into the solution in order to separate the methionine may be applied at room temperature while increasing the pressure until saturation of the solution has occurred.

The mother liquor can be reused for the hydrolysis without any undesirable effects. The hydantoin and, if necessary, water and/or alkali carbonate or alkali bicarbonate are replenished prior to recycling. It is usually only after about 100 runs that a large enough amount of contamination or split-off products, such as homoserine, have accumulated in the mother liquor and the methionine is no longer obtained by precipitation in an adequate degree of purity necessitiating the disposal of the mother liquor.

It is however preferably to proceed by removing in each run a fraction of 1 or 2% of the mother liquor. This fraction is saturated at as low a temperature as possible with carbon dioxide in order to separate out the formed methionine and bicarbonate and it is also reacted with twice or three times the amount of a water-soluble solvent such as an alcohol, preferably methanol or most preferably acetone. The solvent is then recovered by distillation from the final liquor that remains after the filtration.

The following examples will further illustrate the invention.

EXAMPLE 1

A circulated mother liquor contained 327 g of water, 60 g of potassium carbonate, 27 g of potassium bicarbonate, 20 g of methionine and 0.2 g of 5-($\beta$-methylmercaptoethyl)-hydantoin. Into this type of circulating mother liquor 314 g of an aqueous solution were added containing 86 g of the same hydantoin.

The mixture was placed in an autoclave provided with a stirring device and was heated to 170° C and maintained at this temperature for 40 minutes. The pressure was 7 atm. above atmospheric (7atm. of gauge pressure). During this time there were withdrawn by evaporation 212 g of a mass comprising water vapor, ammonia and carbon dioxide. This mass was collected and the completion of the reaction could be determined by the fact that no further ammonia was being discharged.

The solution after release of pressure and cooling to 100° C was then reacted with 0.2 g of activated carbon and after further cooling to 15° C was subjected to filtration. From the filtrate methionine was precipitated by introduction of carbon dioxide. The introduction was effected in a first stage at normal pressure and in a second stage at a pressure of 3 atm. above atmospheric pressure. There were 40 g of carbon dioxide taken up by the solution and the pH went down from 11.5 to 7.5. The precipitated methionine was subjected to filtration and washing with 100 g of water. There were thus obtained 73 g of methionine corresponding to a yield of 99% of the theoretical yield relative to the initial amount of hydantoin. The methionine contained 0.5% of potassium bicarbonate as contamination.

After filtration there were obtained 584 g of mother liquor which were concentrated by evaporation by driving off 130 g of water and 20 g of carbon dioxide. The mother liquor then had about the same composition as the initial solution. The mother liquor was then used again for hydrolysis of hydantoin as above described.

In order to keep the mother liquor intended for hydrolysis of fresh hydantoin constant and in order to avoid an accumulation of byproducts, 10 g of mother liquor were split off prior to each rerun and were separately treated. To recover the dissolved methionine and carbonates the separated mother liquor portion was cooled to 10° C, reacted with twice its amount of acetone and saturated with carbon dioxide at normal pressure. From 10 g of mother liquor there were obtained 0.4 g methionine and 2.2 g potassium bicarbonate which products were reintroduced into the circulation. The mother liquor after distillative recovery of the acetone was discarded.

From the vapors driven off during the hydrolysis an ammonium carbonate solution was recovered. This was used for preparing the hydantoin solution from $\beta$-methylmercaptopropionaldehyde and hydrocyanic acid. Excess carbon dioxide or the carbon dioxide that was obtained due to concentration of the mother liquor were also reused for the methionine precipitation.

EXAMPLE 2

1200 ml of a solution was prepared in which 110 g of potassium carbonate and 50 g of methionine were dissolved. To this solution were added 285 ml of an aqueous solution in which 81 g of 5-($\beta$-methylmercaptoethyl)-hydantoin were contained. The mixture was heated for 4 hrs. at 135° to 140° C at a pressure of 2 to 3 atm. above atmospheric pressure while every hour 150 to 170 ml of an aqueous ammonia solution together with carbon dioxide evaporated.

To separate the methionine the same treatment was applied as in Example 1. By introduction of carbon dioxide into the solution the pH was lowered from 11.6 to 7.6.

There were thus obtained 69 g of methionine which corresponded to a yield of 99.5% relative to the initial amount of hydantoin. The methionine was 99.4% pure and had a melting point between 272° and 273° C.

The total mother liquor was again used for further hydrolysis as described in Example 1. After 50 runs the methionine was still obtained in the same degree of purity as during the first hydrolysis. To remove undesirable byproducts the total amount of mother liquor was then treated by addition of acetone as also described in Example 1. One recovered 94% of dissolved methionine and potassium bicarbonate.

EXAMPLE 3

The treatment was the same as in Example 2, however the initial solution of 1200 ml contained 220 g of potassium bicarbonate and 55 g of methionine. The reaction was carried out in 3½ hours at 140° to 145° C and a pressure between 4.5 and 5.5 atm. above atmospheric. The yield and purity of the methionine which was recovered was the same as in Example 2.

EXAMPLE 4

30 liter of a solution were prepared which contained 1600 g of sodium methioninate and 2360 g of sodium bicarbonate. 1620 g of 5-(β-methylmercaptoethyl)-hydantoin in 5 liter water were added to this solution. The solution was heated for 4 hours to 145° to 150° C. The pressure at the beginning of the reaction was between 4.5 and 5 atm. above normal and at the end of the reaction was between 1 and 1.5 atm. above normal pressure. Each hour 3 to 3.2 liter of an aqueous ammonia solution in addition to carbon dioxide were removed by distillation.

The solution after cooling to 15° C was diluted with water to obtain a volume of 25 liters. By introduction of carbon dioxide methionine was then precipitated. The pH value of the solution thus went down from 11.2 to 7.4 and after introduction of carbon dioxide at 3 atm. above atmospheric was 7.3. The mother liquor was used for further runs as described in Examples 1 and 2.

There were obtained 1360 g of methionine corresponding to a yield of 98.4% relative to the initial hydantoin. The methionine had a purity of 99.5%.

EXAMPLE 5

In this Example a continuously operating pressure apparatus was used which comprised three pressure resistant circulation evaporators arranged in series. A solution of 100 kg potassium bicarbonate, 28 kg methionine and 41 kg of 5-(β-methylmercaptoethyl)-hydantoin in 400 liter water was hourly fed into the apparatus by means of a dosing device.

The solution was continuously replenished from the circulating mother liquor by addition of a 30% concentration solution of 5-(β-methylmercaptoethyl)-hydantoin in water. For a quantitative reaction there was necessary at 155° to 160° C an average residence time of 2 to 2½ hours and at 175° to 180° C an average residence time of 15 to 20 minutes.

In order to remove the formed ammonia and carbon dioxide, 70 to 100 kg of water vapor were passed each hour into the reaction at a temperature of 160° C or 180° C. The further treatment was generally as described in Example 1.

Each hour there were obtained 34.8 kg methionine which corresponded to a yield of 99.1% relative to the initial amount of hydantoin.

About the same results were obtained if nitrogen was used instead of water vapor in order to remove the ammonia and carbon dioxide.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A continuous process for the production of methionine comprising the steps of
   1. hydrolyzing 5-(2-methylmercaptoethyl)hydantoin in an aqueous solution of an alkali-metal carbonate or bicarbonate or mixture thereof at a superatmospheric pressure and at a temperature between 120° and 220° C while
   2. removing the ammonia and carbon dioxide formed during the hydrolysis;
   3. after completion of the hydrolsis reaction cooling the solution;
   4. precipitating the methionine by means of carbon dioxide and separating and recovering the methionine from the remaining mother liquor;
   5. replenishing the mother liquor containing the alkali metal carbonate or bicarbonate and residual methionine with fresh 5-(2-methylmercaptoethyl)hydantoin and then
   6. recycling the replenished mother liquor including residual methionine for further hydrolysis and treatment as in steps 1 to 5.

2. The process of claim 1 wherein the ammonia and carbon dioxide are driven off by passing water vapor or an inert gas through the reaction mass during the hydrolsis.

3. The process of claim 2 wherein the inert gas is nitrogen.

4. The process of claim 1 wherein the mother liquor after the recovery of the bulk of the methionine is concentrated by evaporation to drive off residual water and carbon dioxide prior to said recycling.

5. The process of claim 1 in which the alkali-metal carbonate or alkali-metal bicarbonate is a carbonate or bicarbonate of potassium.

6. The process of claim 1 in which the ratio of 5-(2-methylmercaptoethyl)hydantoin to alkali-metal carbonate or bicarbonate is between 1:1 and 1:5.

7. The process of claim 1 in which the ratio of 5-(2-methylmercaptoethyl)hydantoin to alkali-metal carbonate or bicarbonate is between 1:2 and 1:3.

8. The process of claim 1 in which, in order to remove accumulated contaminations or byproducts from the process, a minor portion of the mother liquor is withdrawn prior to recycling whereupon it is cooled, diluted with a water-miscible solvent and saturated with carbon dioxide whereby the residual methionine and alkali-metal bicarbonate are precipitated and thus freed from the contaminations or byproducts after which they were reintroduced into the circulation.

9. The process of claim 8 wherein the solvent is methanol or acetone.

10. The process of claim 8 wherein the amount of water-miscible solvent is 2 to 3 times that of the removed mother liquor.

11. The process of claim 1 further comprising, during said step of cooling, contacting said solution with activated carbon and subsequently subjecting said solution to filtration, wherein said step of precipitating comprises precipitating the methionine from the filtrate.

* * * * *